United States Patent [19]

Blythin et al.

[11] Patent Number: 4,775,686

[45] Date of Patent: Oct. 4, 1988

[54] NAPHTHYRIDINE DERIVATIVES AND METHOD FOR TREATING ALLERGIC REACTIONS

[75] Inventors: David J. Blythin, North Caldwell; Marvin I. Siegel, Woodbridge; Sidney R. Smith, Ridgewood, all of N.J.

[73] Assignee: Schering Corporation, Kenilworth, N.J.

[21] Appl. No.: 943,859

[22] Filed: Dec. 18, 1986

Related U.S. Application Data

[63] Continuation-in-part of Ser. No. 919,345, Oct. 15, 1986, abandoned.

[51] Int. Cl.$^4$ .................... A61K 31/44; A61K 31/50; C07D 471/04
[52] U.S. Cl. .................... 514/300; 514/241; 514/245; 514/250; 514/253; 514/254; 514/256; 514/275; 544/212; 544/215; 544/238; 544/333; 544/350; 544/405; 546/122; 546/123
[58] Field of Search ............... 546/123, 122; 514/300, 514/245, 241, 253, 254, 256, 275; 544/333, 238, 405, 212, 215

[56] References Cited

U.S. PATENT DOCUMENTS

| | | | |
|---|---|---|---|
| 4,103,257 | 7/1978 | Hammond et al. | 260/296 |
| 4,492,702 | 1/1985 | Sherlock | 424/256 |
| 4,649,144 | 3/1987 | Matsumoto et al. | 546/123 |
| 4,652,564 | 3/1987 | Blythen | 514/248 |

FOREIGN PATENT DOCUMENTS

| | | | |
|---|---|---|---|
| 0172058 | 2/1986 | European Pat. Off. | |
| 0231709 | 8/1987 | European Pat. Off. | 546/123 |
| 0232659 | 8/1987 | European Pat. Off. | 546/123 |
| 2567520 | 1/1986 | France | |

OTHER PUBLICATIONS

Chemical Abstracts: Abstract #126345r, vol. 79 (1973).

*Primary Examiner*—Mary C. Lee
*Assistant Examiner*—J. Richter
*Attorney, Agent, or Firm*—Richard C. Billups; James R. Nelson; Stephen I. Miller

[57] ABSTRACT

1-Substituted naphthyridines and pyrido-pyrazines are disclosed which are useful in treating allergic reactions, inflammation, peptic ulcers and hyperproliferative skin diseases and in suppressing the immune response in mammals. Pharmaceutical compositions and methods of treatment employing such compounds are also disclosed.

25 Claims, No Drawings

NAPHTHYRIDINE DERIVATIVES AND METHOD FOR TREATING ALLERGIC REACTIONS

This application is a continuation-in-part of U.S. application Ser. No. 919,345, filed Oct. 15, 1986 now abandoned.

BACKGROUND OF THE INVENTION

This invention relates to certain 1-substituted naphthyridine and pyridopyrazine derivatives which are useful in the treatment of allergies, inflammation, peptic ulcers and hyperproliferative diseases and which suppress the immune response in mammals.

Carboni et al. in *Farmaco, Ed. Sci.*, 1973, 28(9), 722-732 disclose 1-benzyl-7-benzyloxy[1,8]naphthyridin-2-one and other compounds, but indicate that such compounds were tested as antibacterials and found to be inactive.

European published Application No. 0 172 058 discloses certain 1-phenyl-3-alkyl-[1,8]naphthyridin-2-ones as having anti-ulcer, anti-inflammatory and analgesic activities.

SUMMARY OF THE INVENTION

The invention in its first method aspect relates to a method for treating allergic reactions in a mammal which method comprises administering to the mammal an antiallergic effective amount of a compound having structural formula I

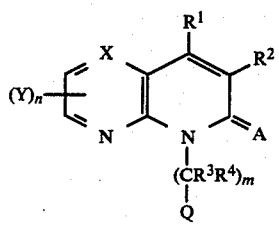

or a pharmaceutically acceptable salt or solvate thereof, wherein:

X represents =CH—, =CY—{wherein Y is as defined below} or =N—;
A represents O or S;
m is an integer of from 0 to 2;
n is an integer of from 0 to 2;
$R^1$ is H, alkyl, halogenated alkyl, cycloalkyl, alkenyl, alkynyl, cycloalkenyl, halo, or —D—Z—$R^5$ {wherein D represents alkanediyl, Z is

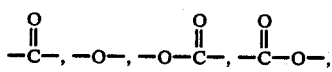

—S(O)$_p$— (wherein p is 0, 1 or 2 with the proviso that p is 0 with $R^5$ is H) or

(wherein $R^6$ is H or alkyl), and $R^5$ is H, alkyl, cycloalkyl, phenyl or phenyl substituted by 1 to 3 Y groups as defined below};
$R^2$ is alkyl or halogenated alkyl;
$R^3$ and $R^4$ are the same or different and each is independently H or alkyl;
Q represents an aryl group or an aromatic heterocyclic group which can optionally be substituted with from 1 to 3 substituents Y as defined below; and
each Y substituent is independently selected from —O$R^6$ {wherein $R^6$ is as defined above}, alkyl, halo, —NO$_2$, —CF$_3$, —CN, cycloalkyl, alkenyloxy, alkynyloxy, —S(O)$_p$—$R^7$ {wherein $R^7$ is alkyl and p is as defined above}, —CO—$R^8$ {wherein $R^8$ represents $R^5$, O$R^6$ or N($R^9$)$_2$ in which $R^5$ and $R^6$ are as defined above and each $R^9$ is independently H or alkyl}, —O—D—CO$R^8$ {wherein D and $R^8$ are as defined above}, —N($R^9$)$_2$ {wherein $R^9$ is as defined above} or —NH(CO)H.

The invention in a second pharmaceutical method aspect is a method for treating hyperproliferative skin diseases, e.g. psoriasis, lichenified eczema or seborrhoeic dermatitis, in a mammal which comprises topically administering an effective amount of a compound of formula I to the mammal.

The invention is a third pharmaceutical method aspect is a method for suppressing the immune response in a mammal which comprises administering an immunosuppressive effective amount of a compound of formula I to the mammal.

The invention also involves novel compounds of structural formula II

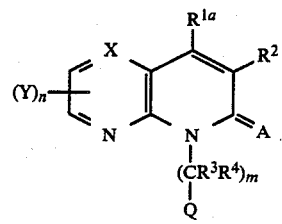

or a pharmaceutically acceptable salt or solvate thereof, wherein:

X represents =CH—, =CY—{wherein Y is as defined below} or =N—;
A represents O or S;
m is an integer of from 0 to 2;
n is an integer of from 0 to 2;
$R^{1a}$ is alkyl, halogenated alkyl, cycloalkyl, alkenyl, alkynyl, cycloalkenyl, halo, or —D—Z—$R^5$ {wherein D represents alkanediyl, Z is

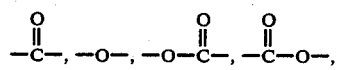

—S(O)$_p$— (wherein p is 0, 1 or 2 with the proviso that p is 0 when $R^5$ is H) or

(wherein $R^6$ is H or alkyl), and $R^5$ is H, alkyl, cycloalkyl, phenyl or phenyl substituted by 1 to 3 Y groups as defined below};
$R^2$ is alkyl or halogenated alkyl;
$R^3$ and $R^4$ are the same or different and each is independently H or alkyl;

Q represents an aryl group or an aromatic heterocyclic group which can optionally be substituted with from 1 to 3 substituents Y as defined below; and each Y substituent is independently selected from —$OR^6$ {wherein $R^6$ is as defined above}, alkyl, halo, —$NO_2$, —$CF_3$, —CN, cycloalkyl, alkenyloxy, alkynyloxy, —$S(O)_p$—$R^7$ {wherein $R^7$ is alkyl and p is as defined above}, —CO—$R^8$ {wherein $R^8$ represents $R^5$, $OR^6$ or $N(R^8)_2$ in which $R^5$ and $R^6$ are as defined above and each $R^9$ is independently H or alkyl}, —O'D—$COR^8$ {wherein D and $R^8$ are as defined above}, —$N(R^9)_2$ {wherein $R^9$ is as defined above} or —NH(CO)H.

The invention in a pharmaceutical composition aspect comprises a compound of formula II in combination with a pharmaceutically acceptable carrier.

The invention in a fourth pharmaceutical method aspect is a method for treating inflammation in a mammal which comprises administering an anti-inflammatory effective amount of a compound of formula II above to the mammal.

The invention in a fifth pharmaceutical method aspect is a method for treating peptic ulcers in a mammal which comprises administering a cytoprotective effective amount of a compound of formula II to the mammal.

Compounds of formulas I and II in which A is oxygen are preferred. Also, X is preferably CH. In formula I $R^1$ is preferably H or alkyl, while in formula II $R^{1a}$ is preferably alkyl. The letters n and m in both formulas I and II preferably represent zero, and Q is preferably phenyl or Y-substituted phenyl, and in the latter case each Y substituent on the Q phenyl ring is preferably independently selected from halo, hydroxy, nitro, alkoxy, alkylthio, $CF_3$, CN or $COR^8$ and more preferably chloro, nitro, methoxy or trifluoromethyl. The most preferred orientation is in the meta position.

A preferred subgenus is represented by the formula Ia or IIa

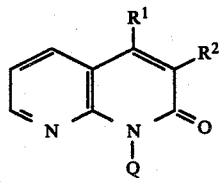

Ia or

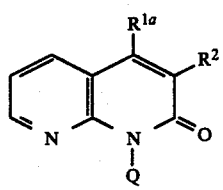

IIa wherein $R^1$ is H or alkyl having from 1 to 4 carbon atoms and $R^{1a}$ is alkyl having from 1 to 4 carbon atoms; $R^2$ is alkyl; and Q is phenyl or phenyl substituted with 1 to 3 Y substituents each independently selected from halo, $NO_2$, OH, alkoxy, alkylthio, $CF_3$, CN or $COR^8$ {wherein $R^8$ is as defined above}.

When utilized herein, the terms below, unless otherwise indicated, have the following scope:

halo-represents fluoro, chloro, bromo and iodo;

alkyl (including the alkyl portions of alkoxy)represents straight or branched carbon chains having from 1 to 6 carbon atoms;

alkanediyl—represents a divalent, straight or branched hydrocarbon chain having from 1 to 6 carbon atoms, the two available bonds being from the same or different carbon atoms thereof, e.g., methylene, ethylene, ethylidene, —$CH_2CH_2CH_2$—,

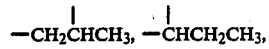

etc.;

halogenated alkyl—represets an alkyl group as defined above having from 1 to 5 halo groups (preferably chloro or fluoro) replacing some or all of the hydrogens thereon depending on the sites of possible halogenation, e.g. —$CF_3$, —$CH_2Cl$, etc.;

alkenyl and alkenyloxy—represent straight or branched carbon chains having at least one carbon to carbon double bond and having from 3 to 6 carbon atoms, with the proviso that the oxygen of alkenyloxy is not bound to an oletinic bond thereof;

alkynyl and alkynyloxy—represent straight or branched carbon chains having at least one carbon to carbon triple bond and having from 3 to 6 carbon atoms, with the proviso that the oxygen of alkynyloxy is not bound to an acetylenic bond thereof;

cycloalkyl—represents a saturated carbocyclic ring having from 3 to 7 carbon atoms;

cycloalkenyl—represents a carbocyclic ring having from 5 to 8 carbon atoms and one carbon to carbon double bond in such ring;

aryl—represents a carbocyclic group having from 6 to 15 carbon atoms and having at least one benzene ring, with all available substitutable carbon atoms thereof being intended as possible points of attachment to the $(CR^3R^4)_m$ group or to the N atom if m is zero. More preferably, aryl is phenyl or Y-substituted phenyl. Suitable aryl groups include, e.g., phenyl, 1-or 2-naphthyl, indenyl, indanyl, 3-chlorophenyl, 4-chlorophenyl, 4-fluorophenyl, etc.;

aromatic heterocyclic—represents cyclic groups having at least one O, S and/or N interrupting a carbocyclic ring structure and having a sufficient number of delocalized pi electrons to provide aromatic character, with the aromatic heterocyclic groups having from 2 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6- [1,2,4-triazinyl], 3- or 5-[1,2,4-thiadiazolyl], 2-, 3-, 4-, 5-, 6 or 7-benzofuranyl, 2-, 3-, 4-, 5-, 6- or 7-indolyl, 3-, 4- or 5-pyrazolyl, 2-, 4- or 5-oxazolyl, etc., with all available substitutable carbon atoms thereof being intended as a possible point of attachment to the $(CR^3R^4)_m$ group or to the N atom if m is zero.

DETAILED DESCRIPTION OF THE INVENTION

The compounds of formulas I and II contain a —$(CR^3R^4)_m$—substituent wherein each $R^3$ group and each $R^4$ group may vary independently. Thus, for example, when m equals 2, the following patterns of substitution (wherein hydrogen and CH₃ are used to represent any substituent, R³ or R⁴, are contemplated:
—C(CH₃)₂CH₂—, —CH₂C(CH₃)₂—, —CH₂CH(CH₃)—, —CH(CH₃)CH₂—, —(C(CH₃)H)₂— and the like.

As noted above, the compounds of formulas I and II may include one to three Y substituents on the fused ring system. Also, the Q group may include up to three Y substituents depending upon the available sites for substitution. In compounds where there is more than one such Y substituent, they may be the same or different. Thus, compounds having combinations of different Y substituents are contemplated within the scope of the invention. Examples of suitable Y substituents include hydroxy, methyl, chloro, bromo, methoxy, cyclohexyl, allyloxy, 2-propynyloxy, methylthio, methylsulfonyl, carboxy, acetoxy, N-methylaminocarbonyl, and the like.

Compounds of formulas I and II can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of formulas I and II may exist in isomeric forms. The invention contemplates all such isomers both in pure form and in admixture, including racemic mixtures.

Certain compounds of formulas I and II also form pharmaceutically acceptable salts with organic and inorganic acids, e.g., the pyrido- or pyrazino-nitrogen atoms may form salts with strong acid, while compounds having basic Y substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

Also, some compounds of formulas I and II are acidic, e.g., when Y is OH, and can form salts with inorganic and organic bases.

The compounds of formulas I and II (note that $R^1$ encompasses $R^{1a}$) may be prepared by a number of different synthetic routes. For example, compounds of formula I wherein $R^1$ is other than halo may be prepared by the methods identified as processes A-E below, while compounds of formula I wherein $R^1$ is halo may be prepared by the process F below:

A. A compound of formula III below is reacted with a compound of formula IV, preferably in excess:

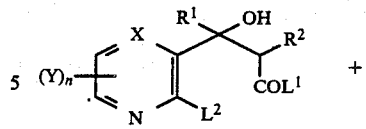

III

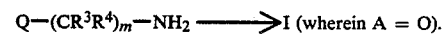

IV $L^1$ represents a suitable leaving group such as halo (e.g., chloro or bromo) or alkoxy. Alternatively, $R^2$ and $L^1$ in the group

together form a lactone ring of the formula

wherein D' represents alkanediyl containing from 2 to 4 carbon atoms. Such lactone ring will cleave to form compounds of the invention wherein $R^2$ is a hydroxyalkyl group. $L^2$ also represents a suitable leaving group such as halo, e.g., chloro or bromo. The reaction may be performed in an inert solvent such as Dowtherm ® (which is a mixture of diphenyl ether and biphenyl) or may be run neat using the amine of formula IV as the "solvent". The amine is used in equivalent amounts or in excess and any suitable temperature can be employed, e.g., 60° C. to reflux. The reaction (and all the reactions herein described) may be followed by thin layer chromatography to determine the course of the reaction.

The compounds of formula III are either known or easily prepared by reacting a compound of formula V with a carbanion of formula VI:

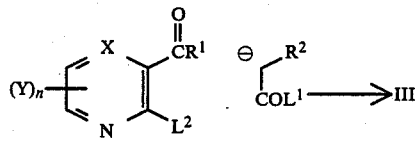

V            VI

This reaction can, for example, be performed in an inert solvent such as tetrahydrofuran (THF) at any suitable temperature, e.g., about −100° C. to about −20° C.

B. A compound of formula V is reacted with a compound of formula VII in the presence of a base such as potassium tertiary butoxide, NaH/DMF, NaH/DMSO/THF, lithium diisopropylamide (LDA)/THF, lithium hexamethyldisilazide/THF, etc., first at a lower suitable temperature such as about −70° C. to about −20° C. and then at a higher suitable temperature as described below:

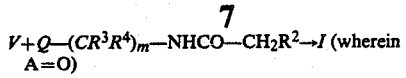  VII wherein $L^2$ of the compound of formula V is as defined above. The base generates an anion in the compound of formula VII. The reaction is normally run in a suitable inert solvent such as dimethyl acetamide (DMA), hexamethyl phosphoric triamide, or those mentioned above with regard to process A. The higher temperature can be, e.g., about 60° C. to about 180° C.

The compounds of formula VII are known or can be prepared by conventional techniques from the appropriately substituted amines of the formula

  (IV)

such as benzyl amine, 3-amino-pyridine, 3-aminofurane, 6-amino-benzofuran, or 4-amino-pyrazine, by reaction with an appropriately substituted acid derivative of the formula $L^3COCH_2R^2$  VIIb wherein $L^3$ is a suitable leaving group, e.g., compound VIIb is the acid chloride or anhydride derivative.

C. A compound of formula VIII is reacted with a compound of formula IX to produce a compound of formula I wherein $R^1$ represents H and A is O:

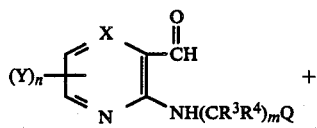

VIII

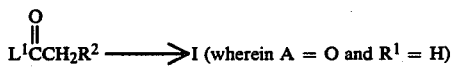

IX wherein $L^1$ is as defined above. The reaction is performed in the presence of base such as tertiary butoxide, sodium ethoxide, etc. The reaction may be performed neat (i.e., with the compound of formula IX as "solvent") or in an inert solvent such as toluene and any suitable temperature may be employed, e.g., 0° to 80° C., The compounds of formula VIII can be prepared by reacting a compound of formula X with an appropriate substituted amine of formula XI:

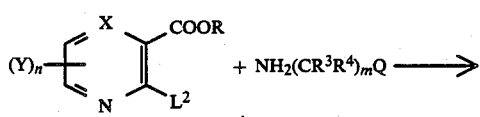

X         XI

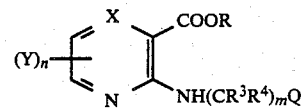

XII wherein $L^2$ is a leaving group as defined above such as chloro or bromo and R is H or alkyl. The compound of formula XII is reduced to the alcohol of formula XIII below by reaction with a strong reducing agent which will reduce a carboxylic acid or ester to the corresponding alcohol, such as Super Hydride (which is triethylborohydride in THF).

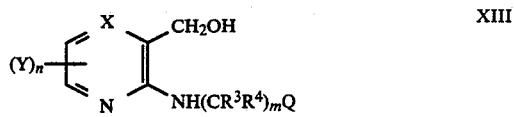

XIII

The compound of formula XIII is then oxidized to the aldehyde of formula VIII above by reaction with a suitable oxidizing agent such as $MnO_2$ in benzene or toluene, for example, at about 80° C.

D. A compound of the formula XV is reacted with a strong acid to eliminate —OH and —$R^{2a}$ from the indicated 4- and 3-positions, respectively, wherein $R^{2a}$ is a group which will eliminate in preference to the desired $R^{2b}$ group, wherein $R^{2b}$ is $R^2$ or a group which may be converted to $R^2$ subsequent to the elimination, e.g., allyl.

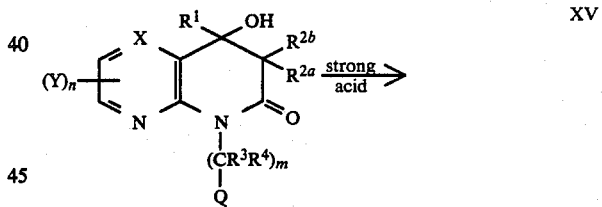

XV

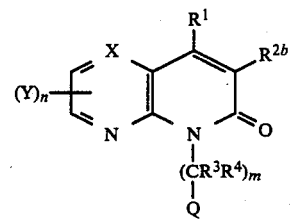

For example, $R^{2a}$ may be a group of formula XVI

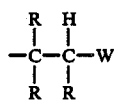  XVI wherein each R may be H or alkyl and W is H, alkyl or a group which enhances the lability of the hydrogen on the beta-carbon atom (thus potentiating the elimination of the $R^{2a}$ group). W can thus be, for example,

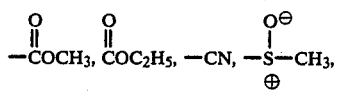

etc. In general, if $R^{2b}$ and $R^{2a}$ both include a hydrogen on the carbon atom beta relative to the naphthyridine or pyridopyrazine nucleus, i.e., both have the basic partial structure

the group with the most labile hydrogen on such beta carbon atom will eliminate in preference to the other group, but a mixture of compounds having $R^2$ or $R^{2a}$ in the 3-position may be obtained, which may be separated by convention means such as chromatography or crystallization. If $R^{2b}$ is allyl (or a similar alkenyl group having the carbon-carbon double bond beta to the naphthyridine or pyridopyrazine nucleus), the hydrogen on the beta carbon atom is less labile and therefore elimination of such an $R^{2b}$ group will be minimized and such $R^{2b}$ group can be converted to $R^2$ by, e.g. conventional hydrogenation, after the elimination of the $R^{2a}$ group.

The reaction may be conducted at any suitable temperature, e.g., $-20°$ C. to $40°$ C. It can be run neat using the acid as a solvent or in an inert solvent such as $CH_2Cl_2$. The acid is preferably a strong acid such as a super acid. Suitable acids include $CF_3SO_3H$, Eaton's reagent, polyphosphoric acid, $HF/BF_3$, etc.

The compounds of formula XV above in which $R^1$ is H (referred to below as formula XVa) may be prepared, for example, by reacting a compound of formula XVIIa or XVIIb

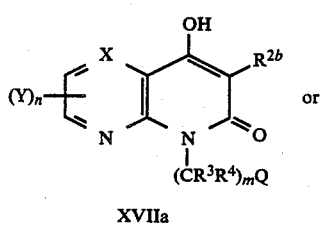

XVIIa

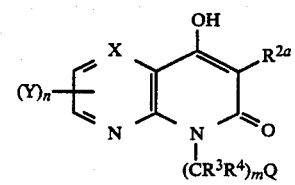

XVIIb (which are either known or can be prepared by the processes described in U.S. Pat. No. 4,492,702) with a compound of the formula $R^{2a}L^5$ or $R^2L^5$, respectively:

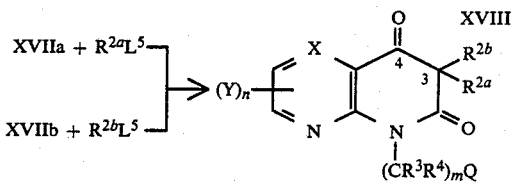

wherein $L^5$ is a suitable leaving group such as halo, e.g., bromo or chloro. The compound of formula XVIII is formed possibly along with its O-alkylated isomers (where $R^{2b}$ or $R^{2a}$ is an alkyl group) which isomers may be separated by chromatography and/or crystallization. The carbonyl in the 4-position of formula XVIII is then reduced to a hydroxy group by employing a suitable reducing agent such as t-butylamine borane to provide a compound of formula XVa.

For preparing compounds of formula XV wherein $R^1$ represents the group $R^{1a}$, a compound of the formula XVIII above is reacted with a suitable Grignard reagent and then dilute acid:

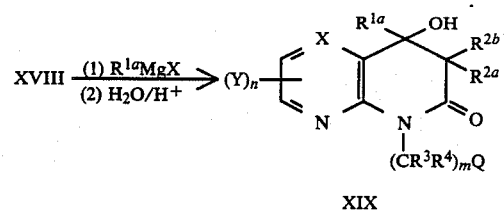

The compound of formula XIX is then reacted with strong acid as described above to eliminate $-R^{2a}$ and $-OH$.

E. A compound of the formula XX is reacted with a strong acid so as to rearrange the $R^{1a}$ group from the indicated 3-position to the 4-position with elimination of $H_2O$:

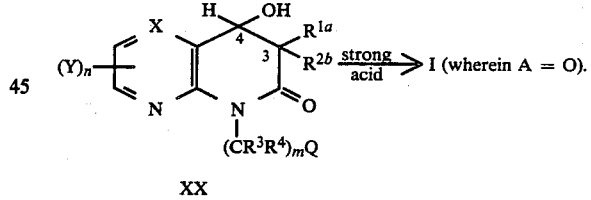

Preferably, $R^{1a}$ and $R^{2b}$ in this rearrangement reaction are both methyl or neither $R^{1a}$ or $R^{2b}$ represents an alkyl chain of 2 or more carbon atoms that has a hydrogen on the carbon atom beta to the naphthyridine or pyridopyrazine nucleus, i.e., neither the $R^{1a}$ nor $R^{2b}$ group has a partial structure

If both $R^{2a}$ and $R^{2b}$ have the structure described in the preceding sentence, the elimination reaction of process D above will compete with the rearrangement described in this process E and a mixture of compounds of formula I from the elimination and rearrangement will result. Thus, in this rearrangement $R^{2b}$ preferably has no such hydrogen on such a beta carbon atom, e.g., as in —CH₃, —CH₂—C(CH₃)₃, etc., or has a hydrogen on the beta carbon which will minimize elimination, e.g., $R^{2b}$ is allyl or another alkenyl group with the carbon-carbon double bond beta to the naphthyridine or pyridopyrazine nucleus. The reaction conditions for process E are basically as described above for process D.

F. To prepare compounds of formula I wherein $R^1$ represents halo, a compound of formula XXI is reacted with a halogenating reagent such as POCl₃, POBr₃, PCl₅, PCl₃, PBr₃, etc.:

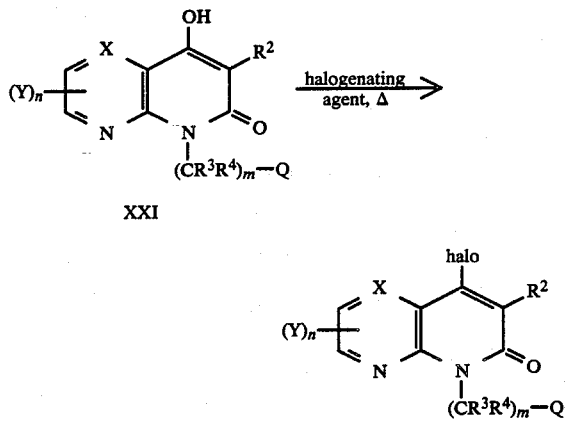

XXI wherein halo is, for example, bromo or chloro. The reaction may be performed at any suitable temperature, but preferably at reflux. An inert solvent may also be employed, if desired. A basic catalyst such as dimethyl aniline may be added. The compounds of formula XXI are known or easily prepared by conventional methods, e.g., see U.S. Pat. No. 4,492,702.

The compounds of formulas I and II wherein A is sulfur may be obtained by treating the purified 2-carbonyl compound of formula I or II with thiating reagents well known in the art. Lawesson's Reagent, {2,4-bis(4-methoxyphenyl-1,3-dithia-2,4-diphosphetane-2,4-disulfide} or one of its analogs, in toluene, or phosphorus pentasulfide in pyridine are suitable for this purpose.

In the above processes, it is sometimes desirable and/or necessary to protect certain $R^1$, $R^2$ and/or Y groups during reactions. Conventional protecting groups are operable. For example, the groups in column 1 of the following table may be protected as indicated in column 2 of the table.

| 1. Group to be Protected | 2. Protected Group |
|---|---|
| —COOH | —COOalkyl, —COObenzyl, —COOphenyl |
| \>NH | \>NCOalkyl, \>NCObenzyl, \>NCOphenyl |
| \>CO | 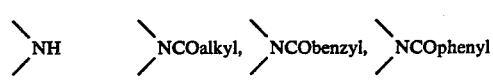 |

| 1. Group to be Protected | 2. Protected Group |
|---|---|
| —OH | 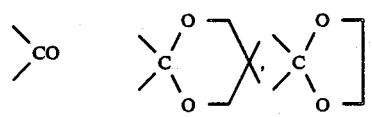 |
| —NH₂ | |

Of course, other protecting groups well known in the art may be used. After the reaction or reactions, the protecting groups may be removed by standard procedures.

Also, certain $R^1$ and Y groups may be converted to other $R^1$ and Y groups by means conventional in the art for such conversions. For example, the $R^1$ group —CH₂CH₂OH may be converted to —CH₂COOH by conventional oxidation with, e.g., pyridinium dichromate.

For preparing pharmaceutical compositions from the compounds described by this invention, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material. In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to about 70% of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically used in the pharmaceutical industries. The term "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution. Aqueous solutions suitable for oral use can be prepared by adding the active component in water and adding suitable colorants, flavoring, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application may include creams, aerosols, sprays, dusts, powders, lotions and ointments which are prepared by combining an active ingredient according to this inventions with conventional pharmaceutical diluents and carriers commonly used in topical dry, liquid, cream and aerosol formulations. Ointments and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g. talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration, for example, liquid preparations containing large amounts of ethanol are not generally suitable for parenteral use.

The compounds of formula I and II may also be deliverable transdermally for systemic distribution. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packaged tablets, capsules and powders in vials or ampules. The unit dosage form can also be a capsule, cachet or tablet itself, or it may be the appropriate number of any of these in a packaged form.

The compounds of formula I may be employed as anti-allergy agents in the treatment of, for example, asthma, allergic or seasonal rhinitis, and/or chronic bronchitis. The anti-allergy method of this invention is identified by tests which measure a compound's inhibition of anaphylactic bronchospasm in sensitized guinea pigs having antigen induced broncho-constriction.

In one such test procedure, male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weigh 450–500 g.

The sensitized guinea pigs are fasted overnight and the following morning are anesthetized with 0.9 ml/kg i.p. of dialurethane (0.1 g/ml diallybarbituric acid, 0.4 g/ml ethylurea and 0.4 g/ml urethane). The trachea are cannulated and the animals are ventilated by a Harvard ® rodent respirator at 50 strokes/minute with a stroke volume of 5 ml. A side arm to the tracheal cannula is connected to a pressure transducer (Harvard) to obtain a continuous measure of intratracheal pressure which is recorded on a polygraph (Harvard). The jugular vein is cannulated for the i.v. administration of substances. The animals are challenged with antigen (0.5% ovalbumin) as an aerosol generated from a DeVilbiss ® Model 65 ultrasonic nebulizer and delivered through the tracheal cannula for 30 seconds. Bronchoconstriction is measured as the peak increase in intratracheal pressure occurring within 5 minutes after antigen challenge.

The sensitized guinea pigs are injected i.v. with 1 mg/kg propranolol, 5 mg/kg indomethacin and 2 mg/kg mepyramine given together in a volume of 1 ml/kg. Fifteen minutes later the animals are challenged with nebulized ovalbumin. Test compounds are administered orally 2 hours before challenge with ovalbumin. Suppression of anaphylactic bronchospasm is expressed as a percent inhibition of the peak increase in intratracheal pressure by comparison to a vehicle-treated control group. In this procedure, 3-methyl-1-phenyl-1,8-naphthyridin-2(1H)-one (referred to as Compound A hereinafter) provided a 96% inhibition at a dose of 5 mg/kg p.o.

The compounds of formula I are also inhibitors of allergen-induced histamine release from guinea pig and human sensitized tissue.

The compounds of formula I are effective non-adrenergic, non-anticholinergic, antianaphylactic agents. They may be administered by any conventional mode of administration by employing an antiallergic effective amount of a compound of formula I for such mode. For example, when administered orally they are active at doses from about 0.5 to 25 mg/kg of body weight, preferably 0.5 to 10 mg/kg; when administered parenterally, e.g., intravenously, the compounds are active at dosages of from about 0.1 to 5 mg/kg body weight preferably 0.1 to 2.5, and when administered by inhalation (aerosol or nebulizer) the compounds are active at dosages of about 0.1 to 5 mg per puff, and one to four puffs may be taken every 4 hours.

The compounds of formula II are also useful for the treatment of inflammation. Thus, they are useful in the treatment of arthritis, bursitis, tendonitis, gout and other physical conditions characterized by inflammation. The anti-inflammatory use of the compounds of formula II may be demonstrated by the Reversed Passive Arthus Response Technique, as described below.

REVERSED PASSIVE ARTHUS RESPONSE (RPAR) ANIMALS, MATERIALS AND METHODS

Male Lewis inbred albino rats weighing 180–200 grams obtained from Charles River Breeding Laboratories are used in these experiments. The rats are housed 3 animals/cage and food and water are allowed ad libitum. The animals are numbered 1–3 in each cage and color marked for identification purposes.

DRUG AND REAGENT PREPARATION

All reagents and drugs are prepared just prior to the study. Crystallized and lyophilized bovine serum albumin (BSA), available from Sigma Chemical Company, is solubilized without shaking in cold, sterile, pyrogen-free saline (10 mg/ml). Lyophilized anti-bovine serum albumin (IgG fraction), obtained from Cappel Laboratories, is suspended in sterile distilled water and diluted with cold, pyrogen-free saline (PFS) just prior to use. The final concentration of anti-bovine serum albumin is 0.5 mg/ml of PFS. Both BSA and anti-BSA solutions are kept near 0° C. during use. Drugs are suspended or solubilized in an aqueous solution of methyl cellulose (MC) with an homogenizer just prior to administration.

DRUG ADMINISTRATION AND INDUCTION OF INFLAMMATION

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared and diluted so as to provide a dose for a 200 gram animal which is equivalent to the mg/kg dose for each experiment. Thus each rat receives an oral dose in a volume of approximately 2.0 cc. One hour after the last dose the animals are lightly anesthetized with ether and "sensitized" by injection of 0.2 ml of PFS containing 1.0 mg of BSA into the penile vein. One hour later, the animals are "challenged" in the right rear paw with subplantar injections of 0.2 ml of ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are subsequently recorded with a plethysmograph during the development of the inflammation at 2 and 4 hours post-challenge.

RESULTS

Results are expressed by the change in paw volume ($\Delta$ paw volume) from the control reading for each animal to that recorded 2 and 4 hours post-challenge. All drug treated groups are compared to the MC control for significant differences with an analysis of variance. Differences from control in drug-treated groups are expressed as percent change from control are determined. Compound A above in this procedure showed a 72% inhibition after 2 hours and a 10% inhibition after 4 hours at a dose (p.o.) of 25 mg/kg.

Another procedure for testing for acute anti-inflammatory activity measures the reverse passive Arthus reaction in the pleural cavity of rats as described in Myers at al., *Inflammation*, Vol. 9, No. 1, 1985, pp. 91–98.

The compounds of formula II can be administered by any conventional mode of administration to obtain the anti-inflammatory activity by employing an anti-inflammatory effective amount of a compound of formula II for such mode. For example, on the basis of the test results, an oral dosage range of from about 5 mg/kg of body weight per day to about 50 mg/kg of body weight per day in divided doses taken at about 4 hour intervals is recommended. The dosage to be administered and the route of administration depends upon the particular compound used, the age and general health of the patient and the severity of the inflammatory condition. Thus, the dose ultimately decided upon must be left to the judgment of a trained health-care practitioner.

The compounds of formula II are also useful in the treatment of peptic ulcers. They possess chemotherapeutic activity which enables them to relieve the symptoms of peptic ulcer disease and stress ulceration, and to promote healing of gastric and/or duodenal ulcers. The antiulcer activity of the compounds of this invention is identified by standard tests which measure the cytoprotective effect in rats, e.g., by inducing gastrointestinal damage with ethanol prior to administering a compound of formula II. The compounds of formula II may be used as conjunctive therapeutic agents for coadministration with such anti-inflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

The compounds of formula II may be evaluated for their antiulcer activity characteristics by the procedures which measure the cytoprotective effect in rats e.g., as described in Chiu et al., *Archives Internationales de Pharmacodynamie et de Therapie*, 270, 128–140 (1984).

In the treatment of peptic ulcer disease, and the prevention and treatment of drug-induced gastric ulceration, the compounds of formula II can be administered in conventional dosage forms such as tablets, capsules, pill, powders, granules, sterile parenteral solutions or suspensions, suppositories, mechanical delivery devices, e.g., transdermal, and the like, again employing a cytoprotective effective amount of a compound of formula II for the mode of administration selected. For example, the compounds of formula II may be administered orally at doses of about 0.3 to about 30 mg/kg, preferably, from about 2 to about 15 mg/kg, of body weight per day. Preferably, the total dosages are administered 2-4 divided doses per day.

The compounds of formula I are useful in the treatment of hyperproliferative skin disease, e.g., psoriasis, which utility may be demonstrated by the Arachidonic Acid Mouse Ear Test as described below.

ARACHIDONIC ACID MOUSE EAR TEST, MATERIALS AND METHODS

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/0.01 ml) and stored at −20° C. for a maximum of 1 week prior to use. Inflammatory reactions are induced by applying 10 μl of AA to both surfaces of one ear (4 mg total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol.* 82, pp 367-371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic.

When administered for the treatment of hyperproliferative skin disease, the compounds of formula I may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at daily doses ranging from about 0.1 mg/kg to about 100 mg/kg, preferably from about 5 mg/kg to about 50 mg/kg, which may be administered in divided doses. When administered rectally, the compounds of formula I may be administered in daily doses ranging from about 0.1 mg/kg to about 100 mg/kg. When administered parenterally, the compounds of formula I are effective for the treatment of hyperproliferative skin disease in daily doses ranging from about 0.1 mg/kg body weight to about 10 mg/kg body weight which may be administered in divided doses.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

Included within the invention are preparation for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, preferably from about 0.1 percent to about 5 percent, is applied several times daily to the affected skin until the condition has improved. Topical applications may then be continued at less frequent intervals (e.g. once a day) to control mitosis in order to prevent return of severe disease conditions.

The compounds of formula I are also useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(F6AF1) male mice are injected intravenously with parental (C57B1/6J) spleen and lymph node cells. A test compound is then administered orally for 10 days beginning on the day prior to the cell transfer. On the day following the last treatment, the animals are sacrificed, and their spleens are excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of the compounds administered to the mice in the experimental group is measured by comparing the spleen weight of the untreated and treated GVH animal with that of the syngeneic control.

SPLENIC ATROPHY

The immunosuppressive activity of the compounds may also be shown by a decrease in spleen weight after dosing BDF$_1$ mice orally with the drug for seven (7) consecutive days. The mice are sacrificed on the eighth day. The percent decrease in spleen weight is measured for each dosage level.

The usual dosage range for the immunosuppressive method of the invention with the compounds of formula I in a 70 kg mammal is an oral dose of about 0.1 to 250 mg/kg, preferably 0.1 to 150 mg/kg, in 3 or 4 divided doses per day. Of course, the dose will be regulated according to the potency of the compound employed, the immunological disease being treated, and the judgment of the attending clinician depending on factors such as the degree and the severity of the disease state and age and general condition of the patient being treated, with an effective amount of a compound of formula I being employed for the particular mode of administration selected.

To treat immunological diseases, the active compounds of formula I can be administered in unit dosage forms such as tablets, capsules, pills, powders, granules, sterile parenteral solutions or suspensions, suppositories, transdermal compositions and the like. Such dosage forms are prepared according to standard techniques well known in the art.

In all of the above modes of treatment, the dosage to be administered and the route of administration depends upon the particular compound selected, the age and general health of the subject, and the severity and type of condition to be controlled. Thus, the dose ultimately provided must be left to the judgment of a trained health-care practitioner.

The quantity of active compound in a unit dose preparation may be varied or adjusted from 1 mg to 100 mg according to the particular application and the potency of the active ingredient and the intended treatment. The composition may, if desired, also contain other therapeutic agents.

When administered parenterally, e.g. intravenously, the compounds are administered at a dosage range of about 0.1 to 5 mg/kg of body weight in single or multiple daily doses.

The invention disclosed herein is exemplified by the following preparative examples, which should not be construed to limit the scope of the disclosure. Alternative mechanistic pathways and analogous structures within the scope of applicants invention, may be apparent to those skilled in the art.

PREPARATIVE EXAMPLE 1

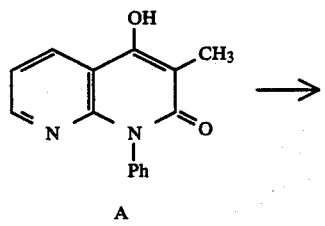

A

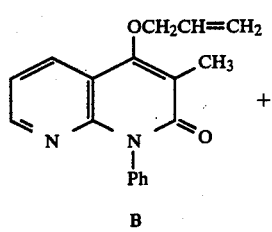

B

+

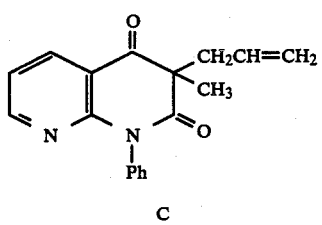

C (wherein Ph = phenyl)

The compound 4-hydroxy-3-methyl-1-phenyl-1,8-naphthyridin-2(1H)-one (10 grams) was suspended in dimethylformamide (250 ml) with $Cs_2CO_3$ (14.2 grams) and the mixture was stirred for about 30 minutes at room temperature. Allyl bromide (4.89 grams) was added and the reaction mixture was stirred for about 1 hour at room temperature. The reaction mixture was poured into 200 ml of distilled water containing 15 ml of glacial acetic acid. The mixture was then extracted with ethylacetate. The extract was dried over $Na_2SO_4$ and filtered and the solvent was evaporated off to give about 9.8 grams of solid which was a mixture of compounds of formulas B and C, predominantly compound B.

The mixture of compounds of formulas B and C above was heated to about 205° C. in an oil bath for about 10 minutes. The conversion of compound B to a compound of formula C (m.p. 110.5°–112° C.) was essentially quantitative.

PREPARATIVE EXAMPLE 2

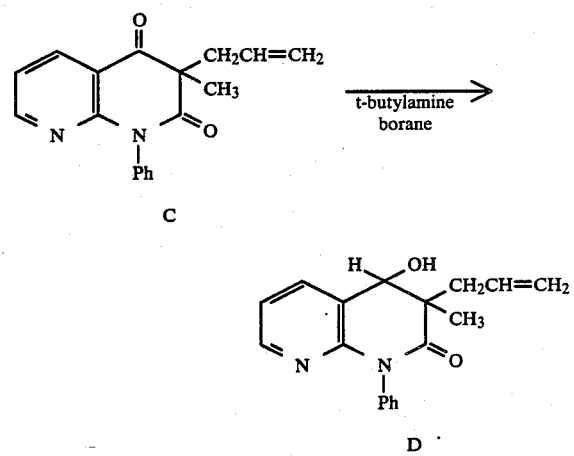

The product of the Preparative Example 1 above (formula C) (2.64 grams) was dissolved in a 1:1 mixture of THF/ethanol (130 ml) under nitrogen. Acetic acid (1.5 ml) was added, followed by t-butylamine-borane (1.4 grams). The reaction was followed by HPLC. After about 1½ hours water (200 ml) was added, the pH was adjusted to about 4.5, and then the mixture was concentrated to a total of about 200 ml. Water (200 ml) was added and the solution was extracted twice with $CH_2Cl_2$. The organic layer was separated and washed twice with saturated sodium chloride solution and the combined organic extracts were dried over $Na_2SO_4$, filtered and concentrated to an oil to provide the desired product of formula D as an oil which was a mixture of diastereomers.

PREPARATIVE EXAMPLE 3

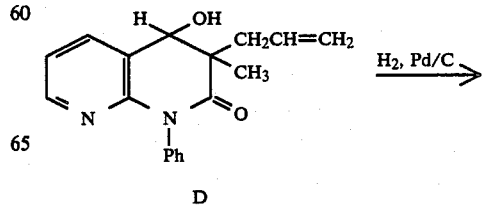

D

-continued

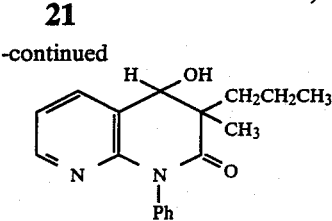

E

The product of Preparative Example 2 above (formula D, 0.5 grams) was dissolved in 20 ml of ethanol and 5% Pd/C (100 mg) in a Paar vessel and hydrogenated for about 1 hour. An additional 400 mg of the 5% Pd/C catalyst was added and the hydrogenation continued for about 4 hours. The reaction mixture was filtered through diatomaceous earth, washed with ethanol and recrystallized from isopropanol to give about 0.435 grams of a compound of formula E, m.p. 172°–174° C.

EXAMPLE 1

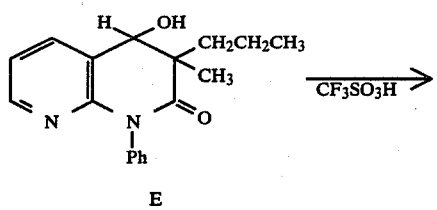

E

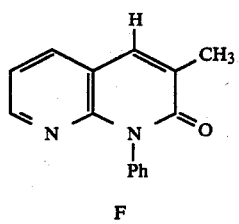

F

The mixture of diastereomers of formula E above from Preparative Example 3 (0.1 grams) was dissolved in CF$_3$SO$_3$H (2 ml) and the mixture was stirred and cooled to about 10° C. for 1 hour. The mixture was then warmed to and maintained at room temperature for 2 days. The reaction mixture was extracted into ethyl acetate, the extract was washed with H$_2$O, dried over Na$_2$SO$_4$, filtered, and the ethyl acetate was evaporated off. The product was recrystallized from isopropanol to give about 0.04 grams of a compound of formula F, m.p. 186°–188° C.

EXAMPLE 2

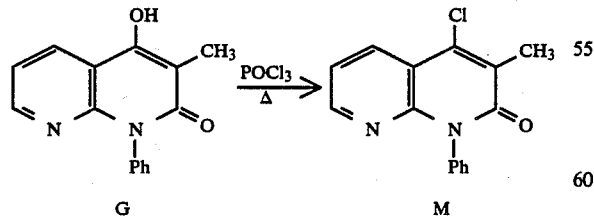

G  M

A compound of formula G above (2.05 grams) was suspended in 10 ml of POCl$_3$ and refluxed for about 4 hours. The remaining POCl$_3$ was distilled off and saturated aqueous NaHCO$_3$ solution was added to the residue. The solid produced was filtered, washed with water, and recrystallized from an isopropanol/water mixture to give a compound of formula M, m.p. 196.5°–197.5° C.

PREPARATIVE EXAMPLE 4

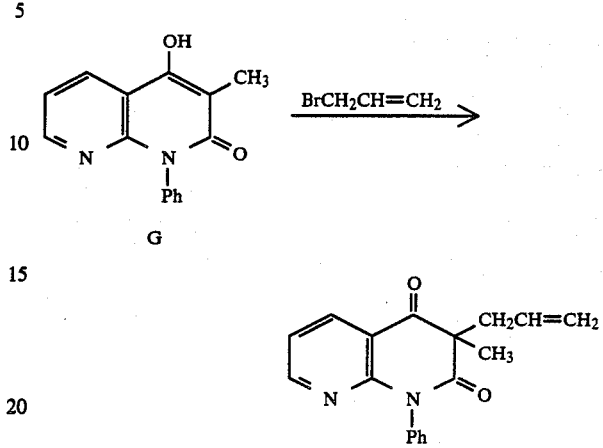

Dissolve 4-hydroxy-3-methyl-1-phenyl-1,8-naphthyridine-2(1H)-one (formula G) (19.4 grams) in dry DMF (500 ml) and add K$_2$CO$_3$ (30 grams). Cool the mixture to about 5° C. and add allylbromide (7 ml) dropwise. Stir the mixture for about 3 hours at about 5° C. and allow to warm to room temperature. Follow the reaction by HPLC. Pour the reaction mixture into H$_2$O (2 liter) containing acetic acid (30 ml). Extract the solution three times with CH$_2$Cl$_2$ (1 liter). Separate and combine the organic layers and wash three times with H$_2$O (500 ml), dry over Na$_2$SO$_4$ and evaporate of the solvent. Heat the product mixture in an oil bath at about 230° C. for about 1 hour to form a compound of formula H.

PREPARATIVE EXAMPLE 5

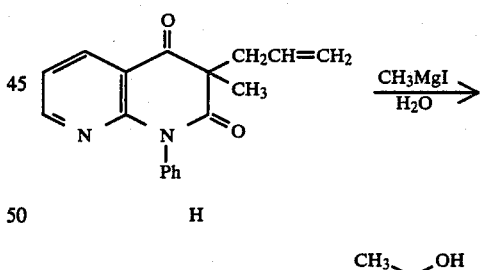

H

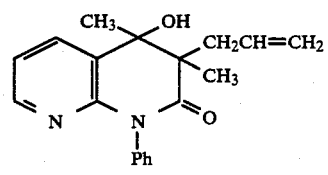

J

Dissolve the product from Preparative Example 4 about (formula H) in dry THF under a nitrogen atmosphere and cool to about 5° C. Add dropwise 2.2 equivalents of CH$_3$MgI in THF with vigorous stirring. Continue stirring until TLC shows no starting material remaining. Add water and adjust the pH to about 5. Extract with CH$_2$Cl$_2$, wash the extract with H$_2$O, dry the extract with Na$_2$SO$_4$, and then filter and evaporate the extract to dryness to yield the desired product of formula J.

PREPARATIVE EXAMPLE 6

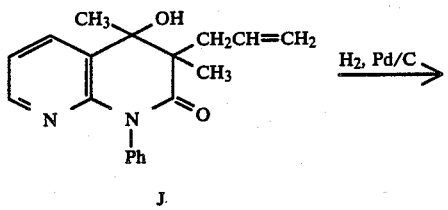

Dissolve the product of Preparative Example 5 (formula J) in about 20 ml of ethanol and add 5% Pd/C (100 mg) in a Paar vessel and hydrogenate for about 1 hour. Add an additional 400 mg of the 5% Pd/C catalyst and continue for about 4 hours, filter through diatomaceous earth, wash with ethanol and concentrate and recrystallize to yield the desired product of formula K.

EXAMPLE 3

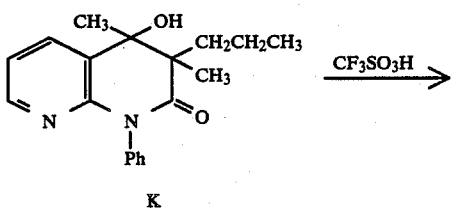

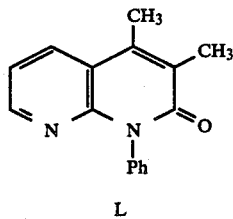

Treat the compound of formula K above in accordance with the procedure set forth in Example 1 above to yield the desired end product of formula L.

The following formulations exemplify some of the dosage forms of the compositions of this invention. In each, the term "active compound" designates 3-methyl-1-phenyl-1,8-naphthyridin-2(1H)-one (Compound A). It is contemplated, however, that this compound may be replaced by equally effective amounts of other compounds of formula I or II where appropriate.

PHARMACEUTICAL DOSAGE FORM EXAMPLES

EXAMPLE A

| No. | Ingredient | Tablets mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

EXAMPLE B

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

| Nasal Spray | mg/ml |
|---|---|
| Active Compound | 10.0 |
| Phenyl Mercuric Acetate | 0.02 |
| Glycine USP | 3.7 |
| Sorbitol Solution, USP | 57.0 |
| Benzalkonium Chloride Solution | 0.2 |
| Sodium Hydroxide 1N Solution to adjust pH |  |
| Water Purified USP to make | 1.0 ml |

The following formulations exemplify some of the dosage forms in which the anti-psoriatic agents of the invention may be employed.

EXAMPLE D

| Ointment Formula | mg/g |
|---|---|
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl 3 alcohol, and cool to 50°–55° C. with stirring. Add the dispersed active compound to the above mixture with stirring. Cool to room temperature.

EXAMPLE E

Cream

| Formula | mg/g |
| --- | --- |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°–40° C. Mix uniformly with stirring and cool to room temperature.

EXAMPLE F

Gel

| Formula | mg./g |
| --- | --- |
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688. |

Method of Manufacture

Prepare a 1% solution of the sodium hydroxide in propylene glycol. Add approximately one-half the remaining propylene glycol and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and mix until a thick gel forms. Dissolve the active compound in the remaining propylene glycol and add to the gel slowly as the gel is continuously mixed.

EXAMPLE G

Lotion

| Formula | mg/g |
| --- | --- |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Method of Manufacture

Prepare a 4% solution of sodium hydroxide in water. Heat the purified water to 60° C. Add carbomer 940 and mix at high speed until dispersed. Cool the above mixture to room temperature and slowly charge sodium hydroxide solution until uniform. Add 80% of isopropyl alcohol to the above with mixing. Dissolve the active compound in remaining isopropyl alcohol. Add this to the mixture with stirring. Adjust pH to 5.0 to 5.5 with sodium hydroxide, if necessary.

EXAMPLE H

Topical Aerosol

| Formula | mg/g |
| --- | --- |
| Active Compound | 1.0–20.0 |
| Caprylic/Capric Triglyceride | 50.00 |
| Mineral Oil | 20.00 |
| Denatured Alcohol | 150.00 |
| Hydrocarbon Aerosol Propellant q.s. ad. | 1.0 g |

Method of Manufacture

Add and mix the caprylic/capric triglyceride mineral oil and specially denatured alcohol in a suitable compounding tank. Add the active compound and continue mixing until the active compound is dissolved or dispersed uniformly. Fill the concentrate into cans and then fill the required amount of hydrocarbon aerosol propellant.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method for treating allergic reactions in a mammal which comprises administering to said mammal an anti-allergy effective amount of a compound having the structural formula I

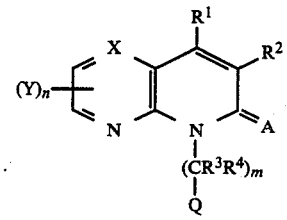

or a pharmaceutically acceptable salt or solvate thereof, wherein:

X represents =CH— or =CY— {wherein Y is defined below};

A represents O or S;

m is an integer of from 0 to 2;

n is an integer of from 0 to 2;

$R^1$ is H, alkyl having from 1 to 6 carbon atoms, halogenated alkyl having from 1 to 6 carbon atoms, cycloalkyl having from 3 to 7 carbon atoms in a saturated carbocyclic ring, alkenyl having from 3 to 6 carbon atoms and having at least one carbon to carbon double bond, alkynyl having from 3 to 6 carbon atoms and having at least one carbon to carbon triple bond, cycloalkenyl having from 5 to 8 carbon atoms in a ring and having one carbon to carbon double bond in the ring, halo, or —D—Z—R$^5$ {wherein D represents alkanediyl having from 1 to 6 carbon atoms and having two available bonds from the same or different carbon atoms, Z is

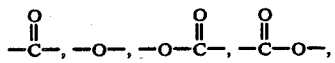

or 2 with the proviso that p is 0 when R$^5$ is H) or

(wherein R$^6$ is H or alkyl having from 1 to 6 carbon atoms), and R$^5$ is H, alkyl having from 1 to 6 carbon atoms, cycloalkyl having from 3 to 7 carbon atoms in a saturated carbocyclic ring, phenyl or phenyl substituted by 1 to 3 Y groups as defined below};

R$^2$ is alkyl having from 1 to 6 carbon atoms or halogenated alkyl having from 1 to 6 carbon atoms and having from 1 to 5 halo groups replacing some or all of the hydrogens thereon;

R$^3$ and R$^4$ are the same or different and each is independently H or alkyl having from 1 to 6 carbon atoms;

Q represents an aryl group having from 6 to 15 carbon atoms and having at least one benzene ring or an aromatic heterocyclic group selected from pyridyl, furyl, thienyl, thiazolyl, imidazolyl, pyrimidinyl, pyrazinyl, pyridazinyl, triazinyl, thiadiazolyl, benzofuranyl, indolyl, pyrazolyl and oxazolyl which aryl or aromatic heterocyclic group can optionally be substituted with from 1 to 3 substituents Y as defined below; and each Y substituent is independently selected from —OR$^6$ {wherein R$^6$ is as defined above}, alkyl having from 1 to 6 carbon atoms, halo, —NO$_2$, —CF$_3$, —CN, cycloalkyl having from 3 to 7 carbon atoms in a saturated carbocyclic ring, alkenyloxy having from 3 to 6 carbon atoms and having at least one carbon to carbon double bond, alkynyloxy having from 3 to 6 carbon atoms and having at least one carbon to carbon triple bond, —S(O)$_p$—R$^7$ {wherein R$^7$ is alkyl having from 1 to 6 carbon atoms and p is as defined above}, —CO—R$^8$ {wherein R$^8$ represents R$^5$, N(R$^9$)$_2$ or OR$^6$ in which R$^5$ and R$^6$ are as defined above and each R$^9$ is independently H or alkyl having from 1 to 6 carbon atoms}, —O—D—COR$^8$ {wherein D and R$^8$ are as defined above}, —N(R$^9$)$_2$ {wherein R$^9$ is as defined above} or —NH(CO)H.

2. A method for treating a mammal suffering from hyperproliferative skin disease which comprises administering to said mammal an anti-hyperproliferative skin disease effective amount of a compound having the structural formula I

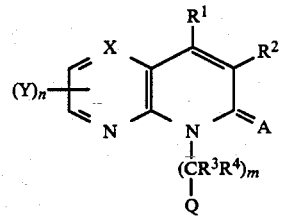

or a pharmaceutically acceptable salt or solvate thereof, wherein:

X represents =CH— or =CY— {wherein Y is defined below};

A represents O or S;

m is an integer of from 0 to 2;

n is an integer of from 0 to 2;

R$^1$ is H, alkyl having from 1 to 6 carbon atoms, halogenated alkyl having from 1 to 6 carbon atoms and having from 1 to 5 halo groups replacing some or all of the hydrogens thereon, cycloalkyl having from 3 to 7 carbon atoms in a saturated carbocyclic ring, alkenyl having from 3 to 6 carbon atoms and having at least one carbon to carbon double bond, alkynyl having from 3 to 6 carbon atoms and having at least one carbon to carbon triple bond, cycloalkenyl having from 5 to 8 carbon atoms in a ring and having one carbon to carbon double bond in the ring, halo, or —D—Z—R$^5$ {wherein D represents alkanediyl having from 1 to 6 carbon atoms and having two available bonds from the same or different carbon atoms, Z is

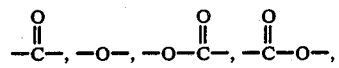

—S(O)$_p$— (wherein p is 0, 1 or 2 with the proviso that p is 0 with R$^5$ is H) or

(wherein R$^6$ is H or alkyl having from 1 to 6 carbon atoms), and R$^5$ is H, alkyl having from 1 to 6 carbon atoms, cycloalkyl having from 3 to 7 carbon atoms in a saturated carbocyclic ring, phenyl or phenyl substituted by 1 to 3 Y groups as defined below};

R$^2$ is alkyl having from 1 to 6 carbon atoms or halogenated alkyl having from 1 to 6 carbon atoms and having from 1 to 5 halo groups replacing some or all of the hydrogens thereon;

R$^3$ and R$^4$ are the same or different and each is independently H or alkyl having from 1 to 6 carbon atoms;

Q represents an aryl group having from 6 to 15 carbon atoms and having at least one benzene ring or an aromatic heterocyclic group selected from pyridyl, furyl, thienyl, thiazolyl, imidazolyl, pyrimidinyl, pyrazinyl, pyridazinyl, triazinyl, thiadiazolyl, benzofuranyl, indolyl, pyrazolyl and oxazolyl which aryl or aromatic heterocyclic group can optionally be substituted with from 1 to 3 substituents Y as defined below; and each Y substituent is independently selected from —OR$^6$ {wherein R$^6$ is as defined above}, alkyl having from 1 to 6 carbon atoms, halo, —NO$_2$, —CF$_3$, —CN, cycloalkyl having from 3 to 7 carbon atoms in a saturated carbocyclic ring, alkenyloxy having from 3 to 6 carbon atoms and having at least one carbon to carbon double bond, alkynyloxy having from 3 to 6 carbon atoms and having at least one carbon to carbon triple bond, —S(O)$_p$—R$^7$ {wherein R$^7$ is alkyl having from 1 to 6 carbon atoms and p is as defined above}, —CO—R$^8$ {wherein R$^8$ represents R$^5$, N(R$^9$)$_2$ or OR$^6$ in which R$^5$ and R$^6$ are as defined above and each R$^9$ is independently H or alkyl having from 1 to 6 carbon atoms}, —O— D-COR$^8$ {wherein D and R$^8$ are as defined above}, —N(R$^9$)$_2$ {wherein R$^9$ is as defined above} or —NH(CO)H.

3. A method for suppressing the immune response in a mammal which comprises administering to said mammal an immunosuppressive effective amount of a compound having the structural formula I

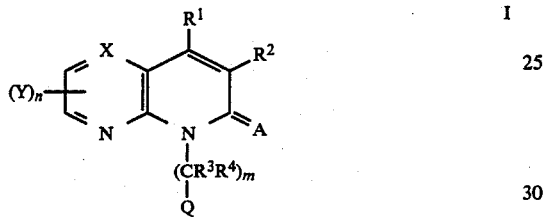

or a pharmaceutically acceptable salt or solvate thereof, wherein:

X represents =CH— or =CY— {wherein Y is defined below};

A represents O or S;

m is an integer of from 0 to 2;

n is an integer of from 0 to 2;

R$^1$ is H, alkyl having from 1 to 6 carbon atoms, halogenated alkyl having from 1 to 6 carbon atoms and having from 1 to 5 halo groups replacing some or all of the hydrogens thereon, cycloalkyl having from 3 to 7 carbon atoms in a saturated carbocyclic ring, alkenyl having from 3 to 6 carbon atoms and having at least one carbon to carbon double bond, alkynyl having from 3 to 6 carbon atoms and having at least one carbon to carbon triple bond, cycloalkenyl having from 5 to 8 carbon atoms in a ring and having one carbon to carbon double bond in the ring, halo, or —D—Z—R$^5$ {wherein D represents alkanediyl containing from 1 to 6 carbon atoms and having two available bonds from the same or different carbon atoms thereof, Z is

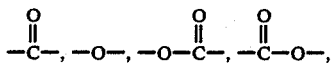

—S(O)$_p$— (wherein p is 0, 1 or 2 with the proviso that when p is 0, R$^5$ is H) or

(wherein R$^6$ is H or alkyl having from 1 to 6 carbon atoms), and R$^5$ is H, alkyl having from 1 to 6 carbon atoms, cycloalkyl having from 3 to 7 carbon atoms in a saturated carbocyclic ring, phenyl or phenyl substituted by 1 to 3 Y groups as defined below};

R$^2$ is alkyl having from 1 to 6 carbon atoms or halogenated alkyl having from 1 to 6 carbon atoms and having from 1 to 5 halo groups replacing some or all of the hydrogens thereon;

R$^3$ and R$^4$ are the same or different and each is independently H or alkyl having from 1 to 6 carbon atoms;

Q represents an aryl group having from 6 to 15 carbon atoms and having at least one benzene ring or an aromatic heterocyclic group selected from pyridyl, furyl, thienyl, thiazolyl, imidazolyl, pyrimidinyl, pyrazinyl, pyridazinyl, triazinyl, thiadiazolyl, benzofuranyl, indolyl, pyrazolyl and oxazolyl which aryl or aromatic heterocyclic group can optionally be substituted with from 1 to 3 substituents Y as defined below; and each Y substituent is independently selected from —OR$^6$ {wherein R$^6$ is as defined above}, alkyl having from 1 to 6 carbon atoms, halo, —NO$_2$, —CF$_3$, —CN, cycloalkyl having from 3 to 7 carbon atoms in a saturated carbocyclic ring, alkenyloxy having from 3 to 6 carbon atoms and having at least one carbon to carbon double bone, alkynyloxy having from 3 to 6 carbon atoms and having at least one carbon to carbon triple bond, —S(O)$_p$—R$^7$ {wherein R$^7$ is alkyl having from 1 to 6 carbon atoms and p is as defined above}, —CO—R$^8$ {wherein R$^8$ represents R$^5$, N(R$^9$)$_2$ or OR$^6$ in which R$^5$ and R$^6$ are as defined above and each R$^9$ is independently H or alkyl having from 1 to 6 carbon atoms}, —O— D—COR$^8$ {wherein D and R$^8$ are as defined above }, —N(R$^9$)$_2$ {wherein R$^9$ is as defined above} or —NH(CO)H.

4. A method according to claim 1 wherein X in formula I represents =CH—.

5. A method according to claim 4 wherein A in formula I is oxygen.

6. A method according to claim 5 wherein m in formula I equals zero.

7. A method according to claim 6 wherein n in formula I equals zero.

8. A method according to claim 7 wherein R$^1$ in formula I is H or alkyl having from 1 to 6 carbon atoms.

9. A method according to claim 8 wherein R$^2$ in formula I is methyl.

10. A method according to claim 7 wherein Q in formula I represents phenyl or Y-substituted phenyl.

11. A method according to claim 9 wherein Q in formula I represents Y-substituted phenyl wherein the 1 to 3 substituents, Y, on the Q phenyl group are each independently selected from halo, hydroxy, nitro, alkoxy having from 1 to 6 carbon atoms, CF$_3$, CN, or COR$^8$.

12. A method according to claim 1 wherein the compound of formula I is 3-methyl-1-phenyl-1,8-naphthyridin-2(1H)-one.

13. A compound having the structural formula II

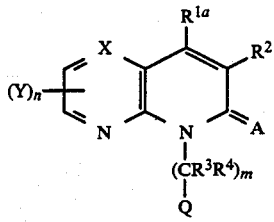

or a pharmaceutically acceptable salt or solvate thereof, wherein:

X represents =CH— or =CY— {wherein Y is defined below};
A represents O or S;
m is an integer of from 0 to 2;
n is an integer of from 0 to 2;
$R^{1a}$ is alkyl having from 1 to 6 carbon atoms, halogenated alkyl having from 1 to 6 carbon atoms and having from 1 to 5 halo groups replacing some or all of the hydrogens thereon, cycloalkyl having from 3 to 7 carbon atoms in a saturated carbocyclic ring, alkenyl having from 3 to 6 carbon atoms and having at least one carbon to carbon double bond, alkynyl having from 3 to 6 carbon atoms and having at least one carbon to carbon triple bond, cycloakenyl having from 5 to 8 carbon atoms in a ring and having one carbon to carbon double bond in the ring, halo, or —D—Z—$R^5$ {wherein D represents alkanediyl having from 1 to 6 carbon atoms and having two available bonds from the same or different carbon atoms thereof, Z is

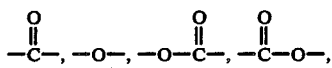

—S(O)$_p$— (wherein p is 0, 1 or 2 with the proviso that p is 0 when $R^5$ is H) or

(wherein $R^6$ is H or alkyl having from 1 to 6 carbon atoms), and $R^5$ is H, alkyl having from 1 to 6 carbon atoms, cycloalkyl having from 3 to 7 carbon atoms in a saturated carbocyclic ring, phenyl or phenyl substituted by 1 to 3 Y groups as defined below};
$R^2$ is alkyl having from 1 to 6 carbon atoms or halogenated alkyl having from 1 to 6 carbon atoms and having from 1 to 5 halo groups replacing some or all of the hydrogens thereon;
$R^3$ and $R^4$ are the same or different and each is independently H or alkyl having from 1 to 6 carbon atoms;

Q represents an aryl group having from 6 to 15 carbon atoms and having at least one benzene ring or an aromatic heterocyclic group selected from pyridyl, furyl, thienyl, thiazolyl, imidazolyl, pyrimidinyl, pyrazinyl, pyridazinyl, triazinyl, thiadiazolyl, benzofuranyl, indolyl, pyrazolyl and oxazolyl which aryl or aromatic heterocyclic group can optionally be substituted with from 1 to 3 substituents Y as defined below; and
each Y substituent is independently selected from alkyl having from 1 to 6 carbon atoms, halo, —NO$_2$, —CF$_3$, —CN, cycloalkyl having from 3 to 7 carbon atoms in an saturated carbocyclic ring, alkenyloxy having from 3 to 6 carbon atoms and having at least one carbon to carbon double bond, alkynyloxy having from 3 to 6 carbon atoms and having at least one carbon to carbon triple bond, —S(O)$_p$—$R^7$ {wherein $R^7$ is alkyl having from 1 to 6 carbon atoms and p is as defined above}, —CO—$R^8$ {wherein $R^8$ represents $R^5$, N($R^9$)$_2$ or OR$^6$ in which $R^5$ and $R^6$ are as defined above and each $R^9$ is independently H or alkyl having from 1 to 6 carbon atoms} or —O—D—COR$^8$ {wherein D and $R^8$ are as defined above}.

14. A compound according to claim 13 wherein X represents =CH—.

15. A compound according to claim 14 wherein A is oxygen.

16. A compound according to claim 15 wherein m equals zero.

17. A compound according to claim 16 wherein n equals zero.

18. A compound according to claim 17 wherein $R^{1a}$ is alkyl having from 1 to 6 carbon atoms.

19. A compound according to claim 18 wherein $R^2$ is methyl.

20. A compound according to claim 17 wherein Q represents phenyl or Y-substituted phenyl.

21. A compound according to claim 19 wherein Q represents Y-substituted phenyl wherein the 1 to 3 substituents, Y, on the Q phenyl group are each independently selected from halo, hydroxy, nitro, alkoxy having from 1 to 6 carbon atoms, CF$_3$, CN, or COR$^8$.

22. A pharmaceutical composition for treating allergy or inflammation comprising an effective amount of a compound of formula II as defined in claim 13 and a pharmaceutically acceptable carrier.

23. A method for treating inflammation in a mammal which comprises administering an anti-inflammatory effective amount of a compound of formula II as defined in claim 13 to said mammal.

24. A method for treating peptic ulcers in a mammal which comprises administering a cytoprotective effective amount of a compound of formula II as defined in claim 13 to said mammal.

25. A method according to claim 2, wherein the compound of formula I is administered topically.

* * * * *